(12) United States Patent
Anzai et al.

(10) Patent No.: US 11,898,131 B2
(45) Date of Patent: Feb. 13, 2024

(54) CELL CULTURE SUBSTRATE HAVING A STRUCTURAL UNIT DERIVED FROM FURFURYL (METH) ACRYLATE

(71) Applicant: TERUMO KABUSHIKI KAISHA, Tokyo (JP)

(72) Inventors: Takao Anzai, Kanagawa (JP); Ichiro Hirahara, Kanagawa (JP)

(73) Assignee: Terumo Kabushiki Kaisha, Tokyo (JP)

( * ) Notice: Subject to any disclaimer, the term of this patent is extended or adjusted under 35 U.S.C. 154(b) by 300 days.

(21) Appl. No.: 16/541,897

(22) Filed: Aug. 15, 2019

(65) Prior Publication Data
US 2020/0056138 A1 Feb. 20, 2020

(30) Foreign Application Priority Data
Aug. 16, 2018 (JP) ................................. 2018-153270

(51) Int. Cl.
C12M 1/12 (2006.01)
C12M 1/00 (2006.01)
C12N 5/00 (2006.01)

(52) U.S. Cl.
CPC ............ C12M 25/14 (2013.01); C12M 23/20 (2013.01); C12N 5/0068 (2013.01); C12N 2533/30 (2013.01)

(58) Field of Classification Search
CPC .. C12N 5/0068; C12N 2533/30; C12M 23/20; C12M 25/14
See application file for complete search history.

(56) References Cited

U.S. PATENT DOCUMENTS

| | | | | |
|---|---|---|---|---|
| 3,726,943 A | * | 4/1973 | Joy ........................ | C08G 77/48 528/26 |
| 3,821,087 A | * | 6/1974 | Knazek et al. ........ | C12M 29/10 435/297.4 |
| 6,225,367 B1 | * | 5/2001 | Chaouk .............. | C08G 18/5015 521/149 |
| 8,168,433 B2 | * | 5/2012 | Gehman .............. | C12N 5/0606 435/402 |
| 8,354,274 B2 | * | 1/2013 | Fadeev ................ | C12N 5/0606 435/366 |
| 2012/0282697 A1 | * | 11/2012 | Henry .................. | C12N 5/0663 524/498 |

FOREIGN PATENT DOCUMENTS

| | | | | |
|---|---|---|---|---|
| EP | 2598518 A1 | * | 6/2013 | ............. C07K 14/78 |
| JP | 2017104028 A | * | 6/2017 | |

OTHER PUBLICATIONS

Lerman et al. The Evolution of Polystyrene as a Cell Culture Material. Tissue Engineering Part B (2018), 24(5), 359-372. (Year: 2018).*
Patel et al. A defined synthetic substrate for serum-free culture of human stem cell derived cardiomyocytes with improved functional maturity identified using combinatorial materials microarrays. Biomaterials (2015), 61, 257-265 (Year: 2015).*
Sato, Chicako; Aoki, Mahiko; Tanaka, Masaru; "Blood-compatible poly (2-methoxyethyl acrylate) for the adhesion and proliferation of endothelial and smooth muscle cells", Colloids and Surfaces B: Biointerfaces, Elsevier B.V. May 18, 2016, pp. 586-596.
Hutcheon et al., "Water absorption and surface properties of novel poly(ethylmethacrylate) polymer systems for use in bone and cartilage repair," Biomaterials, vol. 22, 2001, pp. 667-676.
Official Action (with English translation) for Japan Patent Application No. 2021-502910, dated May 23, 2023, 11 pages.

* cited by examiner

*Primary Examiner* — Sean C. Barron
(74) *Attorney, Agent, or Firm* — Sheridan Ross P.C.

(57) ABSTRACT

To provide a means capable of obtaining further excellent cellular adhesiveness than in a case where a surface of a cell culture substrate (cell culture vessel) is coated using polytetrahydrofurfuryl acrylate (PTHFA).
Provided is a cell culture substrate comprising a coating layer on at least one side of a polymer substrate, wherein the coating layer includes a copolymer comprising more than 20% by mole and less than 100% by mole of a structural unit (1) derived from furfuryl (meth)acrylate represented by Formula (1) and more than 0% by mole and less than 80% by mole of a structural unit (2) derived from ethylenically unsaturated monomer having a hydroxyl group (the total of the structural unit (1) and the structural unit (2) is 100% by mole).

15 Claims, 2 Drawing Sheets

CELL CULTURE SUBSTRATE HAVING A STRUCTURAL UNIT DERIVED FROM FURFURYL (METH) ACRYLATE

TECHNICAL FIELD

The present invention relates to a cell culture substrate excellent in cellular adhesiveness, and a bioreactor and a method for culturing a stem cell using the cell culture substrate.

BACKGROUND

In recent years, a cell culture technology has been used in the development of regenerative medicine or drug discovery. In particular, attention has been paid to use of stem cells, and technology for repairing and replacing damaged or defective tissues has been actively studied by using stem cells expanded from donor cells. Most of cells of animals including humans are adherent (scaffold-dependent) cells which cannot survive in a floating state and survive in a state of being adhered to something. For this reason, various developments of functional culture substrates for culturing adherent (scaffold-dependent) cells at high density to obtain cultured tissues similar to living tissues have been conducted.

As a cell culture substrate, conventionally, plastic (for example: polystyrene) or glass vessels have been used, and it has been reported that a plasma treatment or the like is performed to surfaces of these cell vessels. The substrate subjected to the treatment is excellent in adhesiveness to cells and can proliferously grow cell and maintain the function.

Meanwhile, regarding a structure of the cell culture substrate (cell culture vessel), in addition to a conventional flat dish (plate) structure, various structures, such as a structure in which a porous body is inserted as a culture scaffold in a bag, a hollow fiber structure, a sponge structure, a flocculent (glass wool) structure, and a structure in which a plurality of dishes are laminated, have been developed. It is difficult or impossible to perform plasma irradiation to culture vessels having such diversified and complicated structures.

In this regard, a technique using a polymer that has adhesiveness to cells (cellular adhesiveness) and a property to prompt proliferation of cells (cell proliferation activity) has been proposed. For example, Non Patent Literature 1 discloses that a polymer substrate is coated with a homopolymer of tetrahydrofurfuryl acrylate (PTHFA; polytetrahydrofurfuryl acrylate) to obtain cellular adhesiveness.

CITATION LIST

Non Patent Literatures

Non Patent Literature 1: Colloids and Surfaces B; Biointerfaces 145 (2016) 586-596.

SUMMARY OF THE INVENTION

The polymer such as polytetrahydrofurfuryl acrylate (PTHFA) as disclosed in Non Patent Literature 1 can provide cellular adhesiveness to a cell culture substrate. Further, since such a polymer is excellent in coating operability, even in the case of a cell culture substrate having a complicated structure as described above, the polymer can provide cellular adhesiveness.

However, in a sophisticated cell culturing technique such as providing of cellular adhesiveness to cell culture substrate (cell culture vessels) having various or complicated structures, further improvement in cellular adhesiveness is demanded.

Therefore, the present invention is made in view of the above-described circumstances, and an object thereof is to provide a means capable of obtaining further excellent cellular adhesiveness than in a case where a surface of a cell culture substrate (cell culture vessel) is coated using polytetrahydrofurfuryl acrylate (PTHFA).

The present inventors have conducted intensive studies to solve the above-described problems. As a result, the present inventors have found that the above-described problems can be solved by coating a surface of a cell culture substrate (polymer substrate) using a copolymer containing a structural unit derived from furfuryl (meth)acrylate having a specific structure and a structural unit derived from an ethylenically unsaturated monomer having a hydroxyl group, at a specific composition (molar ratio). The present invention has been completed on the basis of the above finding.

That is, the various objects can be achieved by a cell culture substrate (substrate for cell culture) comprising a coating layer, wherein the coating layer contains a copolymer comprising more than 20% by mole and less than 100% by mole of a structural unit (1) derived from furfuryl (meth)acrylate represented by the following Formula (1) and more than 0% by mole and less than 80% by mole of a structural unit (2) derived from ethylenically unsaturated monomer having a hydroxyl group (the total of the structural unit (1) and the structural unit (2) is 100% by mole).

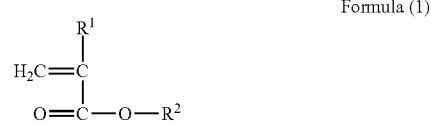

Formula (1)

Wherein, $R^1$ represents a hydrogen atom or a methyl group and $R^2$ represents a group represented by the following Formula (1-1) or the following Formula (1-2):

Formula (1-1)

Formula (1-2)

Wherein, $R^3$ represents an alkylene group having 1 to 3 carbon atoms.

DETAILED DESCRIPTION

Figure 1:
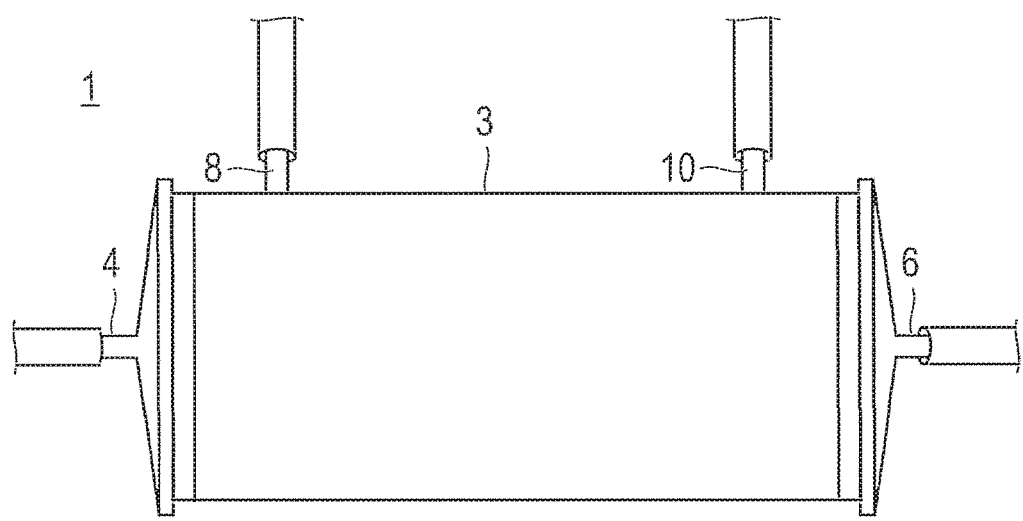
FIG. 1 is a partial side view illustrating an embodiment of a bioreactor (hollow fiber type bioreactor) of the present invention.

A cell culture substrate of the present invention has a coating layer on at least one side of a polymer substrate, wherein the coating layer includes a copolymer comprising more than 20% by mole and less than 100% by mole of a structural unit (1) derived from furfuryl (meth)acrylate represented by the following Formula (1) and more than 0% by mole and less than 80% by mole of a structural unit (2) derived from ethylenically unsaturated monomer having a hydroxyl group (the total of the structural unit (1) and the structural unit (2) is 100% by mole):

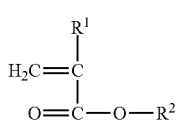

Formula (1)

Wherein, $R^1$ represents a hydrogen atom or a methyl group and $R^2$ represents a group represented by the following Formula (1-1) or the following Formula (1-2):

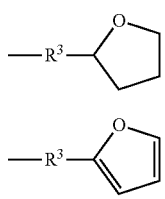

Formula (1-1)

Formula (1-2)

Wherein, $R^3$ represents an alkylene group having 1 to 3 carbon atoms.

With the copolymer according to the present invention, it is possible to provide a means capable of obtaining further excellent cellular adhesiveness than in a case where a surface of a cell culture substrate (cell culture vessel) is coated using polytetrahydrofurfuryl acrylate (PTHFA).

In the present description, the furfuryl (meth)acrylate represented by the above Formula (1) is also simply referred to as the "furfuryl (meth)acrylate" and the structural unit derived from furfuryl (meth)acrylate represented by the above Formula (1) is also simply referred to as the "structural unit (1)." Further, the ethylenically unsaturated monomer having a hydroxyl group is also simply referred to as the "ethylenically unsaturated monomer," and the structural unit derived from ethylenically unsaturated monomer having a hydroxyl group is also simply referred to as the "structural unit (2)." Furthermore, the copolymer having the structural unit (1) and the structural unit (2) is also simply referred to as the "copolymer" or the "copolymer according to the present invention."

Further, in the present description, the term "(meth)acrylate" includes both acrylate and methacrylate". Similarly, the term "(meth)acrylic acid" includes both acrylic acid and methacrylic acid, and "(meth)acryloyl" includes both acryloyl and methacryloyl.

The cell culture substrate of the present invention is characterized in that a coating layer containing the copolymer is formed on at least one side of the polymer substrate. The coating layer (coating film, coating) formed by using the copolymer has favorable cellular adhesiveness as compared to a coating layer formed by using polytetrahydrofurfuryl acrylate (PTHFA). Further, the coating film (coating layer) formed by using the copolymer is also excellent in cell proliferation activity (cell expansion ability). Here, the mechanism for exhibiting the effects by the present invention is presumed to be as follows. Incidentally, the present invention is not limited to the following presumption.

Conventionally, as a means for imparting cell adhesion, there has been a method of applying a cell adhesion factor such as fibronectin, laminin, or collagen to a substrate, a method of subjecting a substrate to treatment with plasma, gamma rays, or electrons, and the like. Of them, the former method has problems in that a cell adhesion factor is expensive and cannot be typically reused since the cell adhesion factor is a natural material, and the like. Further, in the latter method, the plasma treatment can impart particularly excellent cell adhesion to a substrate. Meanwhile, in recent years, a structure in which a porous body is inserted as a culture scaffold in a bag, a hollow fiber structure, a sponge structure, a flocculent (glass wool) structure, and a structure in which a plurality of dishes are laminated are used as a suitable culture scaffold. However, the latter method has a problem in that it is difficult or impossible to apply the method to such diversified and complicated structure. Currently, from the viewpoint that those complicated structures are excellent as a culture scaffold, those complicated structures are demanded as a culture scaffold and a means for providing excellent cellular adhesiveness to such a culture scaffold is demanded.

In view of the circumstances, the present inventors have focused on the fact that a polymer is excellent in coating operability and have conducted intensive studies on a polymer excellent in cellular adhesiveness. In particular, it is known that polytetrahydrofurfuryl acrylate (PTHFA) has cellular adhesiveness as described in Non Patent Literature 1 described above. However, in a sophisticated cell culturing technique, further improvement in cellular adhesiveness is demanded in order to more efficiently perform cell culture.

Therefore, the present inventors have evaluated cellular adhesiveness of polymers and copolymers derived from various monomers, and as a result, have first found that a copolymer of furfuryl (meth)acrylate represented by the above Formula (1) and an ethylenically unsaturated monomer having a hydroxyl group exhibits excellent cellular adhesiveness at a specific composition. Further, the present inventors have also found that these copolymers are excellent in cell proliferation activity (cell expansion ability).

The detailed mechanism thereof is not clear but is presumed that the hydroxyl group (—OH) contained in the structural unit (2) promotes adhesion of cells via activation or induction of signals of adhesion of cells while promoting adhesion of a cell-adhesive protein (cell adhesion factor) to a surface of a coating layer (coating film). Further, it is considered that at this time, when the copolymer forming a coating layer (coating film) contains an appropriate amount of hydroxyl group, a cell adhesion factor such as fibronectin contained in a cell culture solution easily adheres onto the coating layer (coating film), and as a result, cellular adhesiveness is improved.

The present inventors have found that the effect of improving cellular adhesiveness is obtained by the copolymer obtained by further using an ethylenically unsaturated monomer having a hydroxyl group in addition to the furfuryl (meth)acrylate represented by the above Formula (1). Meanwhile, the present inventors have surprisingly found that in a case where the content (ratio) of the structural unit (2) derived from an ethylenically unsaturated monomer having a hydroxyl group is large, cellular adhesiveness is also degraded. Specifically, in the copolymer having the structural unit (1) derived from furfuryl (meth)acrylate and the structural unit (2) derived from an ethylenically unsaturated monomer having a hydroxyl group (the total of the structural unit (1) and the structural unit (2) is 100% by mole), when the content (ratio) of the structural unit (2) is 80% by mole or more, cellular adhesiveness is degraded (Comparative Example 1 described later). The cause for this is not clear, but it is presumed that in a case where the content (ratio) of the structural unit (2) is 80% by mole or more, adhesion onto the coating layer (coating film) of components other than the cell adhesion factor (the components being components not having cellular adhesiveness or having low cellular adhesiveness, for example, albumin contained in the cell culture solution, and the like) becomes more dominant than that of the cell adhesion factor, and the amount of the cell adhesion factor adhered onto the coating layer (coating film) becomes small.

In addition, a hydroxyl group (—OH) of the ethylenically unsaturated monomer having a hydroxyl group which forms the structural unit (2) is presumed to promote expansion (proliferation) of cells via activation or induction of signals of expansion (proliferation) of cells. Therefore, the cell culture substrate according to the present invention is also excellent in cell proliferation activity (cell expansion ability). Incidentally, for example, a homopolymer of hydroxyalkyl (meth)acrylate such as hydroxyethyl methacrylate lowers cellular adhesiveness. From this point, the founding of the present inventors that a copolymer formed by using the ethylenically unsaturated monomer having a hydroxyl group can improve cellular adhesiveness and further cell proliferation activity (cell expansion ability) as compared to a homopolymer of furfuryl (meth)acrylate is very surprising.

Hereinafter, a preferred embodiment of the present invention will be described. Incidentally, the present invention is not limited only to the following embodiment.

In the present description, the term "X to Y" which indicates a range means the term "X or more and Y or less" including X and Y. Further, unless otherwise specified, operations and measurements of physical properties and the like are conducted under conditions of room temperature (20 to 25° C.)/relative humidity of 40 to 50% RH.

<Cell Culture Substrate>

In the cell culture substrate of the present invention, a coating layer containing the copolymer is formed on at least one side of a polymer substrate. The coating layer containing the copolymer according to the present invention has more favorable cellular adhesiveness than a coating layer formed by polytetrahydrofurfuryl acrylate (PTHFA). Further, the coating layer containing the copolymer according to the present invention is also excellent in cell expansion ability (cell proliferation activity). In addition, the coating layer can be simply formed in such a manner that the copolymer is dissolved in a solvent and the resultant solution is applied to a surface of the polymer substrate. Therefore, by using the copolymer according to the present invention, a coating layer (cell adhesion layer) having cellular adhesiveness (and further cell proliferation activity) can be formed on a surface of cell culture substrate (cell culture vessel) regardless of it shape or design.

[Copolymer]

The copolymer according to the present invention has more than 20% by mole and less than 100% by mole of a structural unit (1) derived from furfuryl (meth)acrylate represented by Formula (1) and more than 0% by mole and less than 80% by mole of a structural unit (2) derived from ethylenically unsaturated monomer having a hydroxyl group. Herein, the total of the structural unit (1) and the structural unit (2) is 100% by mole.

The copolymer has the structural unit (1), the structural unit (2), and as necessary, a structural unit derived from other monomer which will be described later in detail. Here, the arrangement of each structural unit is not particularly limited, but may be in the form of block (block copolymer), random (random copolymer), or alternate (alternate copolymer).

The structural unit (1) derived from furfuryl (meth)acrylate provides cellular adhesiveness to a substrate. Further, the structural unit (2) derived from an ethylenically unsaturated monomer having a hydroxyl group included in the copolymer along with structural unit (1) is presumed to promote adhesion of a cell-adhesive protein (cell adhesion factor) to a surface of a coating layer (coating film) by the hydroxyl group thereof. In addition, the structural unit (2) is presumed to provide cell expansion ability (cell proliferation activity) to a substrate by the hydroxyl group thereof. In particular, by combining the furfuryl (meth)acrylate (structural unit (1)) and the ethylenically unsaturated monomer (structural unit (2)) at a specific ratio, more excellent cellular adhesiveness than that of polytetrahydrofurfuryl acrylate (PTHFA) can be provided to a substrate. In addition to the above description, by applying a solution of the copolymer to a surface of a polymer substrate, a coating layer can be simply formed even with respect to substrates having various shapes. Therefore, with the copolymer according to the present invention, a coating layer (cell adhesion layer) excellent in cellular adhesiveness (and further cell proliferation activity) can be formed with respect to cell culture substrates (cell culture vessels) having various shapes or designs.

The structural unit (1) constituting the copolymer according to the present invention is more than 20% by mole and less than 100% by mole with respect to the total (100% by mole) of the structural unit (1) and the structural unit (2), and the structural unit (2) is more than 0% by mole and less than 80% by mole with respect to the total (100% by mole) of the structural unit (1) and the structural unit (2).

Here, when the composition of the structural unit (2) is 80% by mole or more (that is, the composition of the structural unit (1) is 20% by mole or less), the cellular adhesiveness promoting effect (and further cell proliferation activity providing effect) caused by the structural unit (2) is not sufficiently obtained, but also cellular adhesiveness is degraded (comparison between Comparative Example 1 and Comparative Example 2 described later).

From the viewpoint of further improvement in cellular adhesiveness (and further cell proliferation activity), and the like, it is preferable that the structural unit (1) is 35% by mole or more and 98% by mole or less with respect to the total of the structural unit (1) and the structural unit (2), and the structural unit (2) is 2% by mole or more and 65% by mole or less with respect to the total of the structural unit (1) and the structural unit (2). It is more preferable that the structural unit (1) is 40% by mole or more and 95% by mole or less with respect to the total of the structural unit (1) and the structural unit (2), and the structural unit (2) is 5% by mole or more and 60% by mole or less with respect to the total of the structural unit (1) and the structural unit (2). It is further more preferable that the structural unit (1) is 50% by mole or more and 93% by mole or less with respect to the total of the structural unit (1) and the structural unit (2), and the structural unit (2) is 7% by mole or more and 50% by mole or less with respect to the total of the structural unit (1) and the structural unit (2). It is particularly preferable that the structural unit (1) is 55% by mole or more and 90% by mole or less with respect to the total of the structural unit (1) and the structural unit (2), and the structural unit (2) is 10% by mole or more and 45% by mole or less with respect to the total of the structural unit (1) and the structural unit (2). It is most preferable that the structural unit (1) is 60% by mole or more and 90% by mole or less with respect to the total of the structural unit (1) and the structural unit (2), and the structural unit (2) is 10% by mole or more and 40% by mole or less with respect to the total of the structural unit (1) and the structural unit (2).

That is, according to a preferred embodiment of the present invention, the copolymer is a copolymer having 35% by mole or more and 98% by mole or less of the structural unit (1) and 2% by mole or more and 65% by mole or less of the structural unit (2) (the total of the structural unit (1) and the structural unit (2) is 100% by mole). Further, according to a more preferred embodiment of the present invention, the copolymer is a copolymer having 40% by mole or more and 95% by mole or less of the structural unit (1) and 5% by mole or more and 60% by mole or less of the structural unit (2) (the total of the structural unit (1) and the structural unit (2) is 100% by mole). Furthermore, according to a further more preferred embodiment of the present invention, the copolymer is a copolymer having 50% by mole or more and 93% by mole or less of the structural unit (1) and 7% by mole or more and 50% by mole or less of the structural unit (2) (the total of the structural unit (1) and the structural unit (2) is 100% by mole). Furthermore, according to a particularly preferred embodiment of the present invention, the copolymer is a copolymer having 55% by mole or more and 90% by mole or less of the structural unit (1) and 10% by mole or more and 45% by mole or less of the structural unit (2) (the total of the structural unit (1) and the structural unit (2) is 100% by mole). Furthermore, according to a most preferred embodiment of the present invention, the copolymer is a copolymer having 60% by mole or more and 90% by mole or less of the structural unit (1) and 10% by mole or more and 40% by mole or less of the structural unit (2) (the total of the structural unit (1) and the structural unit (2) is 100% by mole).

The copolymer according to the present invention essentially includes the structural unit (1) and the structural unit (2), but may further have a structural unit derived from other monomer in addition to the structural unit (1) and the structural unit (2). Here, the another monomer is not particularly limited as long as it does not inhibit desired characteristics (cell adhesion and/or cell proliferation activity). Specific examples of the another monomer include acrylamide, N,N-dimethylacrylamide, N,N-diethylacrylamide, methacrylamide, N,N-dimethylmethacrylamide, N,N-diethylmethacrylamide, ethylene, propylene, N-vinylacetamide, N-isopropenyl acetamide, N-(meth)acryloyl morpholine, and the like. These other monomers may be used singly or in combination of two or more kinds thereof. The composition of the structural unit derived from other monomer in a case where the copolymer further has a structural unit derived from other monomer is not particularly limited as long as it does not inhibit desired characteristics (cellular adhesiveness and cell proliferation activity), but the structural unit derived from other monomer is preferably more than 0% by mole and less than 10% by mole and more preferably about 3 to 8% by mole with respect to the total of the structural unit (1) and the structural unit (2).

For the purpose of improving cellular adhesiveness (and further cell proliferation activity), it is preferable that the copolymer does not include a structural unit derived from other monomer, that is, the copolymer according to the present invention is configured by only the structural unit (1) and the structural unit (2). That is, according to a preferred embodiment of the present invention, the copolymer is composed of the structural unit (1) and the structural unit (2).

Therefore, according to a more preferred embodiment of the present invention, the copolymer is a copolymer configured by 50% by mole or more and 93% by mole or less of the structural unit (1) and 7% by mole or more and 50% by mole or less of the structural unit (2) (the total of the structural unit (1) and the structural unit (2) is 100% by mole). Further, according to a further more preferred embodiment of the present invention, the copolymer is a copolymer configured by 55% by mole or more and 90% by mole or less of the structural unit (1) and 10% by mole or more and 45% by mole or less of the structural unit (2) (the total of the structural unit (1) and the structural unit (2) is 100% by mole). Further, according to a particularly preferred embodiment of the present invention, the copolymer is a copolymer configured by 60% by mole or more and 90% by mole or less of the structural unit (1) and 10% by mole or more and 40% by mole or less of the structural unit (2) (the total of the structural unit (1) and the structural unit (2) is 100% by mole).

The structural unit (1) is derived from furfuryl (meth)acrylate of the following Formula (1). Incidentally, the structural unit (1) constituting the copolymer may be one kind alone or a combination of two or more kinds thereof. That is, the structural unit (1) may be configured by only one kind of the structural unit derived from furfuryl (meth)acrylate of the following Formula (1) or may be configured by two or more kinds of the structural units derived from furfuryl (meth)acrylate of the following Formula (1). In the latter case, each structural unit may be present in the form of block or random. Further, in a case where the structural unit (1) is configured by two or more kinds of the structural units derived from furfuryl (meth)acrylate of the following Formula (1), the composition of the structural unit (1) is the total ratio (molar ratio (% by mole)) of the furfuryl (meth)acrylate-derived structural units with respect to the total of the structural unit (1) and the structural unit (2).

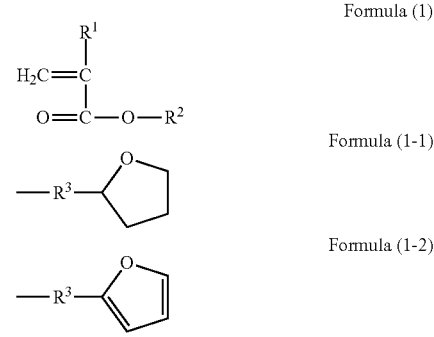

In the Formula (1), $R^1$ is a hydrogen atom or a methyl group.

$R^2$ represents a group represented by the above Formula (1-1) or Formula (1-2). Of them, from the viewpoint of further improvement in cellular adhesiveness (and further cell proliferation activity), and the like, $R^2$ preferably represents a group represented by the above Formula (1-1). In the above Formulae (1-1) and (1-2), $R^3$ represents an alkylene group having 1 to 3 carbon atoms. Herein, as the alkylene group having 1 to 3 carbon atoms, there are a methylene group (—$CH_2$—), an ethylene group (—$CH_2CH_2$—), a trimethylene group (—$CH_2CH_2CH_2$—), and a propylene group (—$CH(CH_3)CH_2$— or —$CH_2CH(CH_3)$—). Among these, from the viewpoint of further improvement in cellular adhesiveness (and further cell proliferation activity), and the like, $R^3$ preferably represents a methylene group (—$CH_2$—) or an ethylene group (—$CH_2CH_2$—) and more preferably represents a methylene group (—$CH_2$—).

That is, as the furfuryl (meth)acrylate, there are tetrahydrofurfuryl acrylate, tetrahydrofurfuryl methacrylate, furfuryl acrylate, furfuryl methacrylate, 5-[2-(acryloyloxy)ethyl]tetrahydrofuran, 5-[2-(methacryloyloxy)ethyl]tetrahydrofuran, 5-[2-(acryloyloxy)ethyl]furane, 5-[2-(methacryloyloxy)ethyl]furane, and the like. These may be used singly or in combination of two or more kinds thereof. Among these, from the viewpoint of further improvement in cellular adhesiveness (and further cell proliferation activity), and the like, tetrahydrofurfuryl (meth)acrylate is preferred and tetrahydrofurfuryl acrylate (THFA) is more preferred.

The structural unit (2) is derived from an ethylenically unsaturated monomer having a hydroxyl group. Incidentally, the structural unit (2) constituting the copolymer may be one kind alone or a combination of two or more kinds thereof. That is, the structural unit (2) may be configured by only one kind of the structural unit derived from ethylenically unsaturated monomer having a hydroxyl group or may be configured by two or more kinds of the structural units derived from ethylenically unsaturated monomer having a hydroxyl group. In the latter case, each structural unit may be present in the form of block or random. Further, in a case where the structural unit (2) is configured by two or more kinds of the structural units derived from ethylenically unsaturated monomer having a hydroxyl group, the composition of the structural unit (2) is the total ratio (molar ratio (% by mole)) of the structural units derived from ethylenically unsaturated monomer having a hydroxyl group with respect to the total of the structural unit (1) and the structural unit (2).

The ethylenically unsaturated monomer having a hydroxyl group which forms the structural unit (2) is not particularly limited as long as it is a compound having one or more hydroxyl groups (—OH) and one or more ethylenically unsaturated groups in one molecule. Herein, the "ethylenically unsaturated group" refers to a group in which a hydrogen atom of ethylene ($CH_2=CH_2$) is substituted, and examples thereof include a (meth)acryloyl group, a vinyl group, an allyl group, a vinyl ether group, and the like. Incidentally, only one of these groups may be contained in one molecule of the ethylenically unsaturated monomer or two or more groups may be contained.

Of them, as the ethylenically unsaturated group, a (meth)acryloyl group is preferred. That is, according to a preferred embodiment of the present invention, the ethylenically unsaturated monomer has a (meth)acryloyl group. Thus, the ethylenically unsaturated monomer is preferably a compound having one or more hydroxyl groups and one or more acryloyl groups or methacryloyl groups in one molecule. The upper limit of the number of hydroxyl groups and (meth)acryloyl groups contained in the ethylenically unsaturated monomer is not particularly limited, but from the viewpoint of controllability of cellular adhesiveness and cell proliferation activity (cell expansion ability), the number of hydroxyl groups in one molecule is preferably 3 or less, more preferably 2 or less, and particularly preferably 1. Further, from the viewpoint of the ease of preparation of the copolymer with furfuryl (meth)acrylate represented by the above Formula (1), controllability of the composition (molar ratio) of each structural unit, and controllability of cellular adhesiveness and cell proliferation activity (cell expansion ability), the number of (meth)acryloyl groups in one molecule is preferably 3 or less and more preferably 2 or less. In particular, from the viewpoint of controlling the composition (molar ratio) of each structural unit to further improve cellular adhesiveness (and further cell proliferation activity), the number of (meth)acryloyl groups in one molecule is particularly preferably 1.

According to a preferred embodiment of the present invention, the structural unit (2) is derived from hydroxyalkyl (meth)acrylate represented by the following Formula (2). That is, the ethylenically unsaturated monomer is preferably hydroxyalkyl (meth)acrylate represented by the following Formula (2). Incidentally, the structural unit (2) constituting the copolymer may be one kind alone or a combination of two or more kinds thereof. That is, the structural unit (2) may be configured by only one kind of the structural unit derived from hydroxyalkyl (meth)acrylate represented by the following Formula (2) or may be configured by two or more kinds of the structural units derived from hydroxyalkyl (meth)acrylate represented by the following Formula (2). In the latter case, each structural unit may be present in the form of block or random. Further, in a case where the structural unit (2) is configured by two or more kinds of the structural units derived from hydroxyalkyl (meth)acrylate represented by the following Formula (2), the composition of the structural unit (2) is the total ratio (molar ratio (% by mole)) of the hydroxyalkyl (meth)acrylate-derived structural units with respect to the total of the structural unit (1) and the structural unit (2).

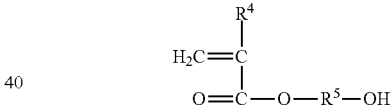

Formula (2)

In the above Formula (2), $R^4$ is a hydrogen atom or a methyl group. $R^5$ is an alkylene group having 2 or 3 carbon atoms. Herein, as the alkylene group having 2 or 3 carbon atoms, there are an ethylene group (—$CH_2CH_2$—), a trimethylene group (—$CH_2CH_2CH_2$—), and a propylene group (—$CH(CH_3)CH_2$— or —$CH_2CH(CH_3)$—). Among these, from the viewpoint of further improving cell adhesion (and further cell proliferation activity), or the like, $R^5$ preferably represents an ethylene group (—$CH_2CH_2$—) or a trimethylene group (—$CH_2CH_2CH_2$—), and more preferably an ethylene group (—$CH_2CH_2$—).

Specifically, examples of hydroxyalkyl (meth)acrylate include hydroxyethyl acrylate, hydroxypropyl acrylate, hydroxyisopropyl acrylate, hydroxyethyl methacrylate, hydroxypropyl methacrylate, hydroxyisopropyl methacrylate, and the like. These may be used singly or in combination of two or more kinds thereof. Among these, from the viewpoint of further improvement in cellular adhesiveness (and further cell proliferation activity), and the like, hydroxyalkyl (meth)acrylate is preferably hydroxyethyl (meth)acrylate and more preferably hydroxyethyl methacrylate (HEMA).

The weight average molecular weight (Mw) of the copolymer is not particularly limited, and is preferably 50,000 to 800,000. Within the above range, the solubility of the copolymer to the solvent is improved and application to the substrate is uniformly conducted with ease. From the viewpoint of improving coating film formability, the weight average molecular weight of the copolymer is more preferably 100,000 to 500,000 and particularly preferably 150,000 to 350,000.

In the present description, as the "weight average molecular weight (Mw)," a value measured by gel permeation chromatography (GPC) using polystyrene as a standard and tetrahydrofuran (THF) as a mobile phase respectively is adopted. Specifically, the copolymer is dissolved in tetrahydrofuran (THF) so as to have a concentration of 10 mg/ml, thereby preparing a sample. Regarding the sample prepared as above, GPC column LF-804 (manufactured by Showa Denko K. K.) is attached to a GPC system LC-20 (manufactured by SHIMADZU CORPORATION), THF is supplied as a mobile phase, and polystyrene is used as a standard, to measure GPC of the copolymer. After preparing a calibration curve with polystyrene as standards, the weight average molecular weight (Mw) of the copolymer is calculated on the basis of the curve.

The copolymer according to the present invention can be produced by employing a conventionally known polymerization method such as bulk polymerization, suspension polymerization, emulsion polymerization, solution polymerization, living radical polymerization method, polymerization method using a macroinitiator, polycondensation method, or the like, for example, although not particularly limited thereto. Specifically, in a case where the copolymer according to the present invention is a block copolymer, for example, a living radical polymerization method or a polymerization method using a macroinitiator is preferably used. As the living radical polymerization method, although not particularly limited thereto, a method described in JP H11-263819 A, JP 2002-145971 A, JP 2006-316169 A, or the like, an atom transfer radical polymerization (ATRP) method, and the like can be applied similarly or appropriately modified, for example.

Alternatively, for example, in a case where the copolymer according to the present invention is a random copolymer, it is preferable to use a method of stirring the furfuryl (meth) acrylate of the above Formula (1), the ethylenically unsaturated monomer having a hydroxyl group (preferably, the hydroxyalkyl (meth)acrylate of the above Formula (2)), and as necessary, one or two or more kinds of monomer which is copolymerizable with those components (other monomer, copolymerizable monomer; the same applies hereinafter), in a polymerization solvent, with a polymerization initiator to prepare a monomer solution, and heating the monomer solution to perform copolymerization. In the method, a polymerization solvent which can be used in the preparation of the monomer solution is not particularly limited as long as it can dissolve the monomer used above. Examples thereof include aqueous solvents such as water, alcohol such as methanol, ethanol, propanol, or isopropanol, and polyethylene glycols; aromatic solvents such as toluene, xylene, and tetralin; halogen-based solvents such as chloroform, dichloroethane, chlorobenzene, dichlorobenzene, and trichlorobenzene; and the like. Among these, taking in consideration of easy dissolution of the monomer, or the like, methanol is preferable. Further, a concentration of the monomer in the monomer solution is not particularly limited, but the concentration of the monomer in the monomer solution is typically 15 to 60% by weight, more preferably 20 to 50% by weight, and particularly preferably 25 to 45% by weight. Incidentally, the concentration of the monomer means the total concentration of the furfuryl (meth)acrylate of the above Formula (1), the ethylenically unsaturated monomer having a hydroxyl group (preferably, the hydroxyalkyl (meth)acrylate of the above Formula (2)), and if being used, a monomer which is copolymerizable with those components (other monomer, copolymerizable monomer).

The polymerization initiator is not particularly limited, and a known polymerization initiator may be used. From the viewpoint of high polymerization stability, the polymerization initiator is preferably a radical polymerization initiator. Specific examples thereof include persulfates such as potassium persulfate (KPS), sodium persulfate, and ammonium persulfate; peroxides such as hydrogen peroxide, t-butyl peroxide, and methyl ethyl ketone peroxide; and azo compounds such as azobisisobutyronitrile (AIBN), 2,2'-azobis (4-methoxy-2,4-dimethylvaleronitrile), 2,2'-azobis(2,4-dimethylvaleronitrile), 2,2'-azobis[2-(2-imidazoline-2-yl) propane]dihydrochloride, 2,2'-azobis[2-(2-imidazoline-2-yl)propane]disulfate dihydrate, 2,2'-azobis(2-methylpropionamidine)dihydrochloride, 2,2'-azobis[N-(2-carboxyethyl)-2-methylpropionamidine)]hydrate, 3-hydroxy-1,1-dimethylbutyl peroxyneodecanoate, α-cumylperoxy neodecanoate, 1,1,3,3-tetrabutyl peroxyneodecanoate, t-butyl peroxyneodecanoate, t-butyl peroxyneoheptanoate, t-butyl peroxypivalate, t-amyl peroxyneodecanoate, t-amyl peroxypivalate, di(2-ethylhexyl)peroxydicarbonate, di(secondary butyl)peroxydicarbonate, and azobiscyanovaleric acid. Further, for example, a reducing agent such as sodium sulfite, sodium hydrogen sulfite, or ascorbic acid may be used in combination with the radical polymerization initiator as a redox type initiator. A blending amount of the polymerization initiator is preferably 0.0005 to 0.005 mol with respect to 1 mol of a total amount of the monomers. With such a blending amount of the polymerization initiator, copolymerization of the respective monomers can efficiently proceed.

The polymerization initiator as it is may be mixed with the furfuryl (meth)acrylate of the above Formula (1), the ethylenically unsaturated monomer having a hydroxyl group (preferably, the hydroxyalkyl (meth)acrylate of the above Formula (2)), and if being used, a monomer which is copolymerizable with those components (other monomer, copolymerizable monomer), and a polymerization solvent, or the initiator in a solution state obtained by the initiator dissolved in another solvent in advance may be mixed with the monomers and the polymerization solvent. In the latter case, another solvent used to dissolve the polymerization initiator is not particularly limited as long as it can dissolve the polymerization initiator, but the same solvent as the polymerization solvent described above can be exemplified. Further, another solvent may be the same as or different from the polymerization solvent, but in consideration of easy control of polymerization, and the like, the same solvent as the polymerization solvent is preferably used. Further, in this case, a concentration of the polymerization initiator in another solvent is not particularly limited, but in consideration of easy mixing, and the like, the addition amount of the polymerization initiator is preferably 0.1 to 10 parts by weight and more preferably 0.5 to 5 parts by weight, with respect to 100 parts by weight of another solvent.

Further, in the case of using the polymerization initiator in the solution state, a deaeration treatment may be performed in advance before adding a solution in which the monomers (furfuryl (meth)acrylate, ethylenically unsaturated monomer having a hydroxyl group, and a copolymerizable monomer which is used optionally) are dissolved in the polymerization solvent, to the polymerization initiator solution. For the deaeration treatment, for example, the solution may be bubbled with an inert gas such as nitrogen gas or argon gas for about 0.5 to 5 hours. In the deaeration treatment, the solution may be adjusted to about 30° C. to 80° C., preferably to a polymerization temperature in a polymerization step as described below.

Next, the monomer solution is heated to copolymerize the respective monomers. Here, as the copolymerization method, for example, a known polymerization method such as radical polymerization, anionic polymerization, or cationic polymerization can be adopted, and radical polymerization which facilitates production is preferably used.

The polymerization conditions are not particularly limited as long as the furfuryl (meth)acrylate of the above Formula (1), the ethylenically unsaturated monomer having a hydroxyl group (preferably, the hydroxyalkyl (meth)acrylate of the above Formula (2)), and if being used, a monomer which is copolymerizable with those components (other monomer, copolymerizable monomer)) can be copolymerized. Specifically, the copolymerization temperature is preferably 30 to 80° C. and more preferably 40° C. to 55° C. Further, the copolymerization time is preferably is 1 to 24 hours and more preferably 5 to 12 hours. Under such conditions, copolymerization of the respective monomers can efficiently proceed. Further, it is possible to effectively suppress or prevent gelation in the polymerization step and to achieve high production efficiency.

As necessary, a chain transfer agent, a polymerization rate-adjusting agent, a surfactant, and other additives may be appropriately used during the polymerization.

An atmosphere under which the polymerization reaction is carried out is not particularly limited, and the reaction can be carried out under an air atmosphere, an inert gas atmosphere such as nitrogen gas or argon gas, and the like. Further, during the polymerization reaction, the reaction solution may be stirred.

The polymer after polymerization can be purified by a general purification method such as a reprecipitation method (precipitation method), a dialysis method, an ultrafiltration method, or an extraction method.

The purified polymer can be dried by an arbitrary method such as freeze drying, vacuum drying, spray drying, or heat drying, but freeze drying or vacuum drying is preferred from the viewpoint that the physical properties of the polymer are less affected.

[Polymer Substrate]

In the present invention, a coating layer containing the copolymer is formed on at least one side of the polymer substrate. Herein, the coating layer is formed on at least a surface of the polymer substrate with which cells contact (for example, on which a liquid containing cells flows or cells are cultured). Further, it is not necessary to form the coating layer on an entire surface of the polymer substrate. The coating layer may be formed on a portion (a part) of the surface of the polymer substrate with which cells contact (for example, on which a liquid containing cells flows or cells are cultured). From the viewpoint of further improving cell adhesion (and further cell proliferation activity), the coating layer is preferably formed on the entire surface of the polymer substrate at the side with which cells contact (for example, on which a liquid containing cells flows or cells are cultured).

Herein, a structure of the polymer substrate is not limited. In addition to the plane structure, the polymer substrate can be designed in various structures (forms) such as a structure in which a porous body is inserted, a hollow fiber structure, a porous membrane structure, a sponge structure, a flocculent (glass wool) structure. As described later, the cell culture substrate of the present invention can be suitably used in a bioreactor, particularly, a hollow fiber type bioreactor. Therefore, the polymer substrate preferably has hollow fibers and is more preferably a porous membrane formed of a plurality of hollow fibers. That is, according to the preferred embodiment of the present invention, the polymer substrate is a porous membrane. In the case where the polymer substrate is a porous membrane, an inner diameter (diameter) of the hollow fiber constituting the porous membrane is not particularly limited, but is preferably 50 to 1,000 µm, more preferably 100 to 500 µm, and particularly preferably about 150 to 350 µm. An outer diameter (diameter) of the hollow fiber constituting the porous membrane is not particularly limited, but is preferably 100 to 1,200 µm, more preferably 150 to 700 µm, and particularly preferably about 200 to 500 µm. A length of the hollow fiber constituting the porous membrane when the polymer substrate is a porous membrane is not particularly limited, but is preferably 50 to 900 mm, more preferably 100 to 700 mm, and particularly preferably about 150 to 500 mm. The number of the hollow fibers constituting the porous membrane when the polymer substrate is a porous membrane is not particularly limited, but is, for example, about 1,000 to 100,000, more preferably 3,000 to 50,000, and particularly preferably about 5,000 to 25,000. In an embodiment, the polymer substrate is configured by about 9,000 hollow fibers having an average length of about 295 mm, an average inner diameter of 215 µm, and an average outer diameter of 315 µm. Herein, the coating layer may be formed on the inner side or the outer side of the hollow fiber membrane, but is preferably formed on the inner (lumen) surface.

A method for producing a hollow fiber and a porous membrane is not particularly limited, and a known production method can be applied similarly or appropriately modified. For example, it is preferable that micro fine holes are formed on a wall of hollow fiber by a stretching method or a solid-liquid phase separation method.

A material constituting the polymer substrate is also not particularly limited. Specific examples thereof include a polyolefin resin such as polypropylene or polyethylene, a hydrophobic polymer material such as polystyrene, polysulfone, polyacrylonitrile, polytetrafluoroethylene, or cellulose acetate, and the like. Further, the polymer substrate may be produced by a semi-permeable, biocompatible polymer material such as a blend of polyamide, polyarylethersulfone, and polyvinylpyrrolidone (PA/PAES/PVP). Such a semi-permeable membrane allows transfer of nutrient, waste, and dissolved gas through the membrane between the extracapillary (EC) space of the hollow fiber and the intracapillary (IC) space of the hollow fiber. The molecule transfer characteristics of the hollow fiber membrane may be selected such that a metabolic waste product can pass through the membrane to be dispersed into a hollow fiber lumen and then removed therefrom, and at the same time, loss of an expensive reagent (such as a growth factor or cytokine) necessary for cell growth from the hollow fiber can be minimized. In a case where the polymer substrate is hollow fibers formed of PA/PAES/PVP, an outer layer of the hollow fiber may have an open pore structure with a certain surface roughness. An opening (diameter) of the pore is not particularly limited, but is in the range of about 0.5 to about 3 µm, and the number of pores on the outer surface of the hollow fiber may be in the range of about 10,000 to about 150,000 per 1 square millimeter (1 mm$^2$). A thickness of the outer layer of the hollow fiber is not particularly limited, and for example, is in the range of about 1 to about 10 µm. The hollow fiber may have an additional layer (second layer) on the outer side, and at this time, the additional layer (second layer) preferably has a sponge structure having a thickness of about 1 to about 15 μm. The second layer having such a structure can serve as a support for the outer layer. Further, in this embodiment, the hollow fiber may have a further additional layer (third layer) at the outer side of the second layer. In this embodiment, the further additional layer (third layer) preferably has a finger-like structure. With the third layer having such a structure, mechanical stability is obtainable. Further, a high void volume with low resistance to membrane transfer of molecules can be provided. In this embodiment, during use, the finger-like voids are filled with fluid and the fluid gives a lower resistance for diffusion and convection than a matrix with a sponge-filled structure having a lower void volume. This third layer has a thickness of, preferably, about 20 to about 60 μm.

Further, the polymer substrate may have about 65% by weight to about 95% by weight of at least a hydrophobic polymer and about 5% by weight to about 35% by weight of at least a hydrophilic polymer. At this time, a total amount of the hydrophobic polymer and the hydrophilic polymer is 100% by weight. Here, the hydrophobic polymer is not particularly limited, and examples thereof include polyamide (PA), polyaramide (PAA), polyarylethersulfone (PAES), polyethersulphone (PES), polysulfone (PSU), polyarylsulphone (PASU), polycarbonate (PC), polyether, polyurethane (PUR), polyetherimide, and polyethersulphone; a mixture of polyarylethersulfone and polyamide; and the like. These hydrophobic polymers may be used singly or as a mixture of two or more kinds thereof. Further, the hydrophilic polymer is not particularly limited, and examples thereof include polyvinylpyrrolidone (PVP), polyethylene glycol (PEG), polyglycolmonoester, water soluble cellulosic derivatives, polysorbate, polyethylene-polypropylene oxide copolymers, and the like. These hydrophilic polymers may be used singly or as a mixture of two or more kinds thereof.

A method of forming a coating layer containing the copolymer according to the present invention on a surface of the polymer substrate is not particularly limited. For example, in a case where the surface of the polymer substrate has a flat dish (plate) structure, a method of applying a copolymer-containing solution obtained by dissolving the copolymer according to the present invention to a predetermined surface (for example, by adding to a well) and then drying coating film can be used. Further, for example, in a case where the polymer substrate is a hollow fiber or a porous membrane, a method of bringing a copolymer-containing solution obtained by dissolving the copolymer according to the present invention into contact with a cell contact portion of the hollow fiber (for example, by flowing on an inner surface (lumen) or an outer surface of the hollow fiber) and then drying coating film can be used. Incidentally, in a case where the polymer substrate is a porous membrane formed by a plurality of hollow fibers, coating with a copolymer-containing solution may be performed with respect to one hollow fiber and then the hollow fibers may be bundled, or a plurality of hollow fibers are bundled to produce a porous membrane and then the coating may be performed.

Herein, a solvent for dissolving the copolymer according to the present invention is not particularly limited as long as it can dissolve the copolymer according to the present invention. From the viewpoint of solubility of the copolymer, and the like, for example, aqueous solvents such as water, alcohol such as methanol, ethanol, propanol, or isopropanol, and polyethylene glycols; ketone-based solvents such as acetone; furan-based solvents such as tetrahydrofuran; and the like are exemplified. The solvent may be used singly or in the form of a mixture of two or more kinds thereof. Among these, in consideration of further improvement in solubility of the copolymer according to the present invention, the solvent is preferably a mixed solvent of water and alcohol. The alcohol used in the mixed solvent is preferably lower alcohol having 1 to 4 carbon atoms from the viewpoint of improving solubility of the copolymer, particularly, methanol or ethanol is preferred and ethanol is particularly preferred. That is, the solvent is preferably configured by water and ethanol. Herein, the mixing ratio of water and ethanol is not particularly limited, and for example, the mixing ratio (volume ratio) of water and ethanol is preferably 1:1 to 50 and more preferably 1:5 to 15. A concentration of the copolymer in the copolymer-containing solution is not particularly limited. In consideration of the ease of application to the substrate, the effect of reducing coating unevenness, and the like, the concentration thereof is preferably 0.0001 to 5% by weight more preferably 0.001 to 2% by weight.

Further, a method of coating the copolymer is not particularly limited, and a conventionally known method such as filling, dip coating (immersion method), spraying, spin coating, dropping, doctor blade, brush coating, roll coater, air knife coating, curtain coating, wire bar coating, gravure coating, or mixed solution-impregnated sponge coating can be applied.

Further, conditions for forming the coating film of the copolymer are not particularly limited. For example, a contact time of the copolymer-containing solution and the polymer substrate (for example, a time for circulating the copolymer-containing solution to a lumen or an outer surface of the hollow fiber) is preferably 1 to 5 minutes and more preferably 1 to 3 minutes, in consideration of the easy formation of the coating film (thus coating layer), the effect of reducing coating unevenness, and the like. Further, a contact temperature of the copolymer-containing solution and the polymer substrate (for example, a temperature at which the copolymer-containing solution is circulated to a lumen or an outer surface of hollow fiber) is preferably 5 to 40° C. and more preferably 15 to 30° C., in consideration of the easy formation of the coating film (thus coating layer), the effect of reducing coating unevenness, and the like.

The amount of the copolymer-containing solution applied to the surface of the polymer substrate is not particularly limited, but is preferably such an amount that the thickness of the coating layer after drying is about 0.005 to 20 μm. Incidentally, in a case where the above-described thickness is not obtainable by single contact (application), a contact (application) step (or the application step and a drying step described later) may be repeated until a desired thickness is obtainable.

Next, by drying the coating film after the contact of the polymer substrate and the copolymer-containing solution, the coating layer (coating film) by the copolymer according to the present invention is formed on the surface of the polymer substrate. Herein, drying conditions are not particularly limited as long as the coating layer (coating film) of the copolymer according to the present invention can be formed. Specifically, a drying temperature is preferably 5 to 50° C. and more preferably 15 to 40° C. A drying step may be performed under a single condition or may be performed stepwise under different conditions. Further, a drying time is preferably 60 to 480 minutes and more preferably 120 to 300 minutes. Further, in a case where the polymer substrate is a porous membrane (hollow fiber membrane), the coating film may be dried by allowing a gas of 5 to 40° C. and more preferably 15 to 30° C. to continuously or gradually circulate on a surface of hollow fiber to which the copolymer-containing solution is applied. Herein, the gas is not particularly limited as long as it has no influence on the coating film (coating layer) and can dry the coating film. Specific examples thereof include air, an inert gas such as nitrogen gas or argon gas, and the like. Further, a circulation amount of the gas is not particularly limited as long as the coating film can be sufficiently dried. The circulation amount of the gas is preferably 5 to 150 L/min and more preferably 30 to 100 L/min.

According to such a method, the copolymer according to the present invention can be efficiently formed on the polymer substrate. Incidentally, depending on the type of cells to be adhered, the polymer substrate may be further treated with a cell adhesion factor such as fibronectin, laminin, or collagen. With such a treatment, adhesion of cells to the substrate surface and growth of cells can be further promoted. In a case where the polymer substrate is a porous membrane formed of a plurality of hollow fibers, the treatment with a cell adhesion factor may be performed with respect to one hollow fiber and then the hollow fibers may be bundled, or a plurality of hollow fibers are bundled to produce a porous membrane and then the treatment may be performed. Further, the treatment with a cell adhesion factor may be performed after the coating layer containing the copolymer according to the present invention is formed, before the coating layer containing the copolymer according to the present invention is formed, or at the same time the coating layer containing the copolymer according to the present invention is formed.

<Bioreactor>

The cell culture substrate of the present invention shows excellent cell adhesion. Further, the cell culture substrate of the present invention has cell proliferation activity. Therefore, the cell culture substrate of the present invention can be suitably used in a bioreactor. That is, the present invention provides a bioreactor including the cell culture substrate of the present invention. Here, the bioreactor may be a plane type bioreactor or a hollow fiber type bioreactor, but is particularly preferably a hollow fiber type bioreactor. Therefore, in the following description, although a hollow fiber type bioreactor will be described as a preferred embodiment, the bioreactor of the present invention may be a plane type bioreactor, and in this case, the following embodiment can be appropriately changed and applied. Further, dimensional ratios in the drawings are exaggerated for the sake of explanatory convenience and may differ from actual ratios.

The bioreactor in which the cell culture substrate of the present invention can be suitably used is not particularly limited, but the cell culture substrate and the bioreactor of the present invention can be applied, for example, to cell culture/expansion systems described in JP 2010-523118 A (JP 5524824 B2)(WO 2008/124229 A2), JP 2013-524854 A (JP 6039547 B2) (WO 2011/140231 A1), JP 2013-507143 A (JP 5819835 B2) (WO 2011/045644 A1), JP 2013-176377 A (WO 2008/109674), JP 2015-526093 A (WO 2014/031666 A1), JP 2016-537001 A (WO 2015/073918 A1), JP 2017-509344 A (WO 2015/148704 A1), and the like; and Quantum Cell Expansion System manufactured by TERUMO BCT, INC. Conventionally, in the cell culture, facilities such as an incubator, a safety cabinet, and a clean room are separately needed, but the culture system as described above has all of those functions so that the facilities can be very simplified. Further, by controlling temperature or gas during the cell culture using the system as described above, a functionally closed system can be ensured and the cell culture can be performed automatically and in a closed environment.

Hereinafter, an embodiment of the bioreactor of the present invention will be described with reference to the drawings, but the present invention is not limited to the following embodiment.

Figure 2:
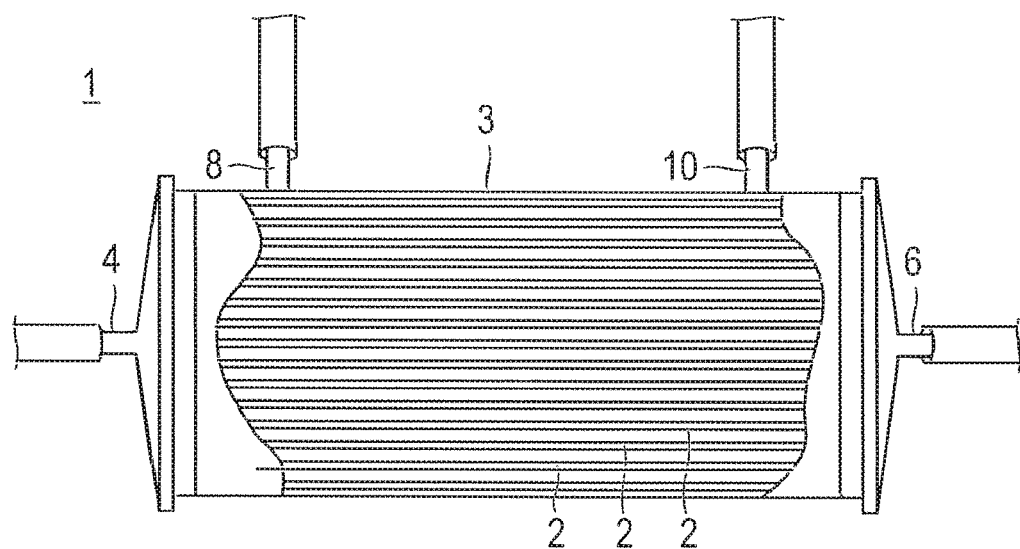
FIG. 2 is a partially cut-away side view of the bioreactor of FIG. 1.

FIG. 1 is a partial side view illustrating an embodiment of a bioreactor (hollow fiber type bioreactor) of the present invention. Further, FIG. 2 is a partially cut-away side view of the bioreactor of FIG. 1. In FIGS. 1 and 2, a bioreactor 1 has a cell culture substrate 2 of the present invention provided in a cell culture chamber 3. The cell culture chamber 3 has four openings, that is, four ports (an inlet port 4, an outlet port 6, an inlet port 8, and an outlet port 10). Herein, a culture medium including cells flows to a hollow fiber intracapillary (IC) space of the cell culture substrate 2 in the cell culture chamber 3 through the inlet port 4, and discharged from the outlet port 6. According to this, cells are efficiently adhered (attached) to and cultured on the surface of the hollow fiber lumen. Meanwhile, a culture medium or gas (such as oxygen or carbon dioxide) flows to be in contact with a hollow fiber extracapillary (EC) space of the cell culture substrate 2 in the cell culture chamber 3 through the inlet port 8, and discharged from the outlet port 10. According to this, in the cell culture chamber 3, small molecules such as culture medium components flow into the hollow fibers or unnecessary components are discharged from the inside of the hollow fibers, and cells adhered onto the surface of the hollow fibers are cultured. Further, after culturing for a predetermined time, a liquid (for example, PBS) containing trypsin is introduced into the intracapillary (IC) space of the hollow fiber of the cell culture substrate 2 in the cell culture chamber 3 through the inlet port 4, and then is held for a predetermined time (for example, about 5 to 10 minutes). Next, a culture medium or an isotonic solution such as PBS flows in the intracapillary (IC) space of the hollow fiber of the cell culture substrate 2 in the cell culture chamber 3 through the inlet port 4 to apply a shear force to cells, the cells are released from the inner wall of the hollow fiber, and the cells are recovered from the bioreactor through the outlet port 6. Incidentally, although the cells are adhered to the intracapillary (IC) space of the hollow fiber in the above embodiment, the present invention is not limited to the above embodiment, and cells may be cultured in such a manner that a culture medium containing cells flows into the outlet port 10 from the inlet port 8, the cells are efficiently adhered (attached) to an outer surface of the hollow fiber, and the culture medium flows into the outlet port 6 from the inlet port 4 in an hollow fiber lumen. Further, the fluid from the inlet port 4 into the outlet port 6 may flow in either a co-current or counter-current direction with respect to flow of fluid into the outlet port 10 from the inlet port 8.

[Use of Bioreactor]

As mentioned above, the bioreactor of the present invention includes a cell culture substrate excellent in cell adhesion (and further cell proliferation activity). Herein, cells which can be cultured in the bioreactor of the present invention may be adherent (scaffold-dependent) cells, non-adherent cells, or any combination thereof. In consideration of excellent cell adhesion (and further cell proliferation activity), the bioreactor of the present invention can be particularly suitably used in culturing of adherent (scaffold-dependent) cells. Herein, as the adherent (scaffold-dependent) cells, there are animal cells such as stem cells including mesenchymal stem cell (MSC) or the like, fibroblast cells, and the like. As mentioned above, attention has been paid to stem cells in development of regenerative medicine or drug discovery. Therefore, the bioreactor of the present invention can be suitably used in culturing of stem cells. That is, the present invention provides a method for culturing a stem cell using the bioreactor of the present invention. Herein, the method for culturing a stem cell is not particularly limited, and a general culturing method can be applied similarly or appropriately modified.

EXAMPLES

The effects of the present invention will be described using the following examples and comparative examples. However, the technical scope of the present invention is not limited to only the following examples. Incidentally, in the following examples, operations were carried out at room temperature (25° C.) unless otherwise specified. In addition, unless otherwise specified, "%" and "part" mean "% by weight" and "parts by weight," respectively.

Production Example 1: Synthesis of Copolymer (1)

To a 20-ml glass pressure-proof test tube, 0.90 g (0.0058 mol) of tetrahydrofurfuryl acrylate (THFA), 1.1 g (0.0085 mol) of hydroxyethyl methacrylate (HEMA), and 3 g of methanol were added, and then nitrogen gas was bubbled for 10 seconds, thereby preparing a monomer solution (1). To this monomer solution (1), 0.004 g (0.013 mmol) of 2,2'-azobis(4-methoxy-2,4-dimethylvaleronitrile) as a polymerization initiator was added, and the resultant mixture was heated in a heat block set at 45° C. for 6 hours, to perform polymerization reaction, thereby obtaining obtain a polymerization liquid (1). This polymerization liquid (1) was added to 50 ml of n-hexane, and the precipitated polymer component was recovered and dried under reduced pressure, thereby obtaining a copolymer of tetrahydrofurfuryl acrylate and hydroxyethyl methacrylate (THFA:HEMA=40:60 (molar ratio)) (copolymer (1)). The weight average molecular weight (Mw) of this copolymer (1) was measured to be 210,000.

Production Example 2: Synthesis of Copolymer (2)

To a 20-ml glass pressure-proof test tube, 1.10 g (0.007 mol) of tetrahydrofurfuryl acrylate (THFA), 0.90 g (0.007 mol) of hydroxyethyl methacrylate (HEMA), and 3 g of methanol were added, and then nitrogen gas was bubbled for 10 seconds, thereby preparing a monomer solution (2). To this monomer solution (2), 0.004 g (0.013 mmol) of 2,2'-azobis(4-methoxy-2,4-dimethylvaleronitrile) as a polymerization initiator was added, and the resultant mixture was heated in a heat block set at 45° C. for 6 hours, to perform polymerization reaction, thereby obtaining a polymerization liquid (2). This polymerization liquid (2) was added to 50 ml of n-hexane, and the precipitated polymer component was recovered and dried under reduced pressure, thereby obtaining a copolymer of tetrahydrofurfuryl acrylate and hydroxyethyl methacrylate (THFA:HEMA=50:50 (molar ratio)) (copolymer (2)). The weight average molecular weight (Mw) of this copolymer (2) was measured to be 230,000.

Production Example 3: Synthesis of Copolymer (3)

To a 20-ml glass pressure-proof test tube, 1.3 g (0.0083 mol) of tetrahydrofurfuryl acrylate (THFA), 0.70 g (0.0054 mol) of hydroxyethyl methacrylate (HEMA), and 3 g of methanol were added, and then nitrogen gas was bubbled for 10 seconds, thereby preparing a monomer solution (3). To this monomer solution (3), 0.004 g (0.013 mmol) of 2,2'-azobis(4-methoxy-2,4-dimethylvaleronitrile) as a polymerization initiator was added, and the resultant mixture was heated in a heat block set at 45° C. for 6 hours, to perform polymerization reaction, thereby obtaining a polymerization liquid (3). This polymerization liquid (3) was added to 50 ml of n-hexane, and the precipitated polymer component was recovered and dried under reduced pressure, thereby obtaining a copolymer of tetrahydrofurfuryl acrylate and hydroxyethyl methacrylate (THFA:HEMA=60:40 (molar ratio)) (copolymer (3)). The weight average molecular weight (Mw) of this copolymer (3) was measured to be 240,000.

Production Example 4: Synthesis of Copolymer (4)

To a 20-ml glass pressure-proof test tube, 1.65 g (0.0106 mol) of tetrahydrofurfuryl acrylate (THFA), 0.35 g (0.0027 mol) of hydroxyethyl methacrylate (HEMA), and 3 g of methanol were added, and then nitrogen gas was bubbled for 10 seconds, thereby preparing a monomer solution (4). To this monomer solution (4), 0.004 g (0.013 mmol) of 2,2'-azobis(4-methoxy-2,4-dimethylvaleronitrile) as a polymerization initiator was added, and the resultant mixture was heated in a heat block set at 45° C. for 6 hours, to perform polymerization reaction, thereby obtaining a polymerization liquid (4). This polymerization liquid (4) was added to 50 ml of n-hexane, and the precipitated polymer component was recovered and dried under reduced pressure, thereby obtaining a copolymer of tetrahydrofurfuryl acrylate and hydroxyethyl methacrylate (THFA:HEMA=80:20 (molar ratio)) (copolymer (4)). The weight average molecular weight (Mw) of this copolymer (4) was measured to be 260,000.

Production Example 5: Synthesis of Copolymer (5)

To a 20-ml glass pressure-proof test tube, 1.83 g (0.0117 mol) of tetrahydrofurfuryl acrylate (THFA), 0.17 g (0.0013 mol) of hydroxyethyl methacrylate (HEMA), and 3 g of methanol were added, and then nitrogen gas was bubbled for 10 seconds, thereby preparing a monomer solution (5). To this monomer solution (5), 0.004 g (0.013 mmol) of 2,2'-azobis(4-methoxy-2,4-dimethylvaleronitrile) as a polymerization initiator was added, and the resultant mixture was heated in a heat block set at 45° C. for 6 hours, to perform polymerization reaction, thereby obtaining a polymerization liquid (5). This polymerization liquid (5) was added to 50 ml of n-hexane, and the precipitated polymer component was recovered and dried under reduced pressure, thereby obtaining a copolymer of tetrahydrofurfuryl acrylate and hydroxyethyl methacrylate (THFA:HEMA=90:10 (molar ratio)) (copolymer (5)). The weight average molecular weight (Mw) of this copolymer (5) was measured to be 250,000.

Production Example 6: Synthesis of Copolymer (6)

To a 20-ml glass pressure-proof test tube, 0.46 g (0.0029 mol) of tetrahydrofurfuryl acrylate (THFA), 1.54 g (0.0118 mol) of hydroxyethyl methacrylate (HEMA, and 3 g of methanol were added, and then nitrogen gas was bubbled for 10 seconds, thereby preparing a monomer solution (6). To this monomer solution (6), 0.004 g (0.013 mmol) of 2,2'-azobis(4-methoxy-2,4-dimethylvaleronitrile) as a polymerization initiator was added, heating was performed by a heat block set at 45° C. for 6 hours, and polymerization reaction was performed, thereby obtaining a polymerization liquid (6). This polymerization liquid (6) was added to 50 ml of n-hexane, and the precipitated polymer component was recovered and dried under reduced pressure, thereby obtaining a copolymer of tetrahydrofurfuryl acrylate and hydroxyethyl methacrylate (THFA:HEMA=20:80 (molar ratio)) (copolymer (6)). The weight average molecular weight (Mw) of this copolymer (6) was measured to be 230,000.

Production Example 7: Synthesis of THFA Polymer (7)

To a 20-ml glass pressure-proof test tube, 2.0 g (0.0128 mol) of tetrahydrofurfuryl acrylate (THFA) and 3 g of methanol were added, and then nitrogen gas was bubbled for 10 seconds, thereby preparing a monomer solution (7). To this monomer solution (7), 0.004 g (0.013 mmol) of 2,2'-azobis(4-methoxy-2,4-dimethylvaleronitrile) as a polymerization initiator was added, and the resultant mixture was heated in a heat block set at 45° C. for 6 hours, to perform polymerization reaction, thereby obtaining a polymerization liquid (7). This polymerization liquid (7) was added to 50 ml of hexane, and the precipitated polymer component was recovered and dried under reduced pressure, thereby obtaining a homopolymer of tetrahydrofurfuryl acrylate (THFA polymer (7)). The weight average molecular weight (Mw) of this THFA polymer (7) was measured to be 290,000.

Production Example 8: Synthesis of HEMA Polymer (8)

To a 20-ml glass pressure-proof test tube, 2.0 g (0.0154 mol) of hydroxyethyl methacrylate (HEMA) and 3 g of methanol were added, and then nitrogen gas was bubbled for 10 seconds, thereby preparing a monomer solution (8). To this monomer solution (8), 0.004 g (0.013 mmol) of 2,2'-azobis(4-methoxy-2,4-dimethylvaleronitrile) as a polymerization initiator was added, and the resultant mixture was heated in a heat block set at 45° C. for 6 hours, to perform polymerization reaction, thereby obtaining a polymerization liquid (8). This polymerization liquid (8) was added to 50 ml of n-hexane, and the precipitated polymer component was recovered and dried under reduced pressure, thereby obtaining a homopolymer of hydroxyethyl methacrylate (HEMA polymer (8)).

Example 1: Coating to Cell Culture Dish

The copolymer (1) obtained in Production Example 1 described above was dissolved in a mixed solvent of water and ethanol (water:ethanol=1:9 (volume ratio)) to have a concentration of 0.05% by weight, thereby producing a coating liquid (1). 25 μL of this coating liquid (1) was added to each well of commercially available 96-well tissue culture polystyrene dish (without a plasma treatment, manufactured by FALCON, trade name: Non-Tissue Culture Treated Plate, 96 Well, Flat Bottom with Low Evaporation Lid) and dried at 20° C. for 300 minutes to produce a polymer coating film (dry thickness: 0.3 μm), thereby obtaining a cell culture dish (1).

Examples 2 to 5: Coating to Cell Culture Dish

A polymer coating film was produced on the well surface according to the similar method to Example 1, except that, in Example 1, each of the copolymers (2) to (5) was used instead of the copolymer (1), thereby obtaining cell culture dishes (2) to (5).

Comparative Examples 1 to 3: Coating to Cell Culture Dish

A polymer coating film was produced on the well surface according to the similar method to Example 1, except that, in Example 1, each of the copolymer (6), the THFA polymer (7), and the HEMA polymer (8) was used instead of the copolymer (1), thereby obtaining comparative cell culture dishes (1) to (3).

Reference Example 1

A commercially available 96-well tissue culture polystyrene dish (without a plasma treatment and a polymer coating film, manufactured by FALCON, trade name: Non-Tissue Culture Treated Plate, 96 Well, Flat Bottom with Low Evaporation Lid) was prepared as a non-treated cell culture dish.

[Evaluation: Cell Culture and Measurement of Adhesion Activity]

Cells were cultured using the cell culture dishes (1) to (5) and the comparative cell culture dishes (1) to (3) obtained in Examples 1 to 5 and Comparative Examples 1 to 3, and the non-treated cell culture dish as Reference Example 1 described above according to the following description and the cell adhesion activity (cellular adhesiveness) was evaluated. Incidentally, as the cells, human adipose tissue-derived mesenchymal stem cells (Lonza, Walkersville, Maryland, U.S.A.) were used. The donor was a 22-year-old man and expressed CD13, CD29, CD44, CD73, CD90, CD105, CD166≥90%, CD14, CD31, and CD45≤5%.

The human adipose tissue-derived mesenchymal stem cells were seeded on each well of each cell culture dish to be $2\times10^3$ cells/well, and then humidified at 37° C. and cultured for one day in Mesenchymal Stem Cell Growth Medium 2 (PromoCell GmbH, Bedford, Massachusetts, U.S.A.) with an incubator in the presence of 5% $CO_2$. After the completion of culture, the culture solution was exchanged with Mesenchymal Stem Cell Growth Medium 2 containing 10% WST-1 (Premix WST-1 Cell Proliferation Assay System, Takara Bio Inc., Shiga, Japan) and then incubated for about 4 hours under normal pressure (37° C., 5% $CO_2$) under humidified conditions. An absorbance (450 nm, comparison 600 nm) of the culture solution was measured by a microplate reader and regarded as cell adhesion activity. Results are presented in the following Table 1.

TABLE 1

| | Polymer | | | | Ratio of adhesion activity to Comparative Example 2 |
|---|---|---|---|---|---|
| | | Monomer type | Monomer composition (Molar ratio) | Cell adhesion activity ($Abs_{450}$) | |
| Example 1 | Copolymer (1) | THFA-HEMA | 40:60 | 0.205 | 1.020 |
| Example 2 | Copolymer (2) | THFA-HEMA | 50:50 | 0.210 | 1.045 |

TABLE 1-continued

| | Polymer | | | Cell adhesion activity ($Abs_{450}$) | Ratio of adhesion activity to Comparative Example 2 |
|---|---|---|---|---|---|
| | | Monomer type | Monomer composition (Molar ratio) | | |
| Example 3 | Copolymer (3) | THFA-HEMA | 60:40 | 0.222 | 1.104 |
| Example 4 | Copolymer (4) | THFA-HEMA | 80:20 | 0.216 | 1.075 |
| Example 5 | Copolymer (5) | THFA-HEMA | 90:10 | 0.218 | 1.085 |
| Comparative Example 1 | Copolymer (6) | THFA-HEMA | 20:80 | 0.184 | 0.915 |
| Comparative Example 2 | THFA polymer (7) | THFA | — | 0.201 | 1.000 |
| Comparative Example 3 | HEMA polymer (8) | HEMA | — | 0.046 | 0.229 |
| Reference Example 1 | — | (Without plasma treatment and without polymer coating film) | | 0.067 | 0.333 |

From the result of the above Table 1, the cell culture dishes in which the polymer coating films are formed using the copolymers (1) to (5) of Production Examples 1 to 5 exhibited higher cellular adhesiveness than the cell culture dish in which the polymer coating film is formed using the homopolymer of THFA (THFA polymer (7)). On the other hand, it was shown that the cellular adhesiveness of the cell culture dishes in which the polymer coating films are formed using the THFA-HEMA copolymer (copolymer (6)) which is out of the composition according to the present invention and the HEMA polymer (8) is degraded more than that of the cell culture dish in which the polymer coating film is formed using the homopolymer of THFA (THFA polymer (7)).

REFERENCE SIGNS LIST

1 BIOREACTOR
2 CELL CULTURE SUBSTRATE
3 CELL CULTURE CHAMBER
4, 8 INLET PORT
6, 10 OUTLET PORT

The invention claimed is:

1. A cell culture substrate comprising a coating layer on at least one side of a polymer substrate,
wherein the coating layer comprises a copolymer having a weight average molecular weight from 50,000 to 800,000 and consisting of at least 60% by mole and no more than 90% by mole of a structural unit (1) and at least 10% by mole and no more than 40% by mole of a structural unit (2),
wherein the structural unit (1) is derived from a furfuryl acrylate monomer of Formula (1):

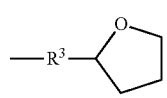

wherein, $R^1$ represents a hydrogen atom or a methyl group and $R^2$ represents a group represented by the following Formula (1-1) or the following Formula (1-2):

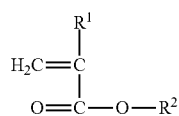

Formula (1-1)

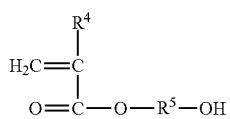

Formula (1-2)

wherein, $R^3$ represents an alkylene group having 1 to 3 carbon atoms, and
wherein the structural unit (2) is derived from an ethylenically unsaturated monomer comprising an acryloyl or meth acryloyl group and a hydroxy group.

2. The cell culture substrate according to claim 1, wherein the ethylenically unsaturated monomer is a hydroxyalkyl acrylate monomer represented by Formula (2):

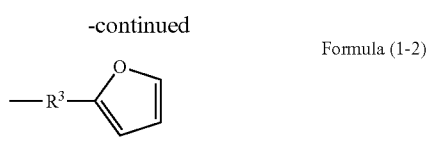

wherein, $R^4$ represents a hydrogen atom or a methyl group and $R^5$ represents an alkylene group having 2 or 3 carbon atoms.

3. The cell culture substrate according to claim 1, wherein the polymer substrate is a porous membrane.

4. A bioreactor comprising the cell culture substrate according to claim 1.

5. A method for culturing a stem cell using the bioreactor according to claim 4.

6. The cell culture substrate according to claim 2, wherein the hydroxyalkyl acrylate monomer is selected from the group consisting of hydroxyethyl acrylate, hydroxypropyl acrylate, hydroxyisopropyl acrylate, hydroxyethyl methacrylate, hydroxypropyl methacrylate, hydroxyisopropyl methacrylate, and two or more combinations thereof.

7. The cell culture substrate according to claim 6, wherein the hydroxyalkyl acrylate monomer is hydroxyethyl methacrylate.

8. The cell culture substrate according to claim 1, wherein the copolymer has a weight average molecular weight from 150,000 to 350,000.

9. The cell culture substrate according to claim 1, wherein the coating layer has a thickness from 0.005 μm to 20 μm.

10. The cell culture substrate according to claim 1, wherein the coating layer consists of the copolymer.

11. The cell culture substrate according to claim 1, wherein the polymer substrate has one or more of a hollow fiber structure, a porous membrane structure, a sponge structure, and a flocculent structure.

12. The cell culture substrate according to claim 1, wherein the polymer substrate comprises hollow fibers having an inner diameter from 50 μm to 1000 μm and a length from 50 mm to 900 mm.

13. The cell culture substrate according to claim 1, wherein the polymer substrate comprises hollow fibers and wherein the coating layer is formed on one or both of an inner surface and an outer surface of the hollow fibers.

14. The cell culture substrate according to claim 3, wherein the porous membrane comprises hollow fibers.

15. The cell culture substrate according to claim 1, wherein the polymer substrate comprises a polymer selected from the group consisting of: polypropylene, polethylene, polystyrene, polysulfone, polyacrylonitrile, polytetrafluoroethylene, cellulose acetate, polyamide, polyarylethersulfone, polyvinylpyrrolidone, and mixtures of two or more thereof.

* * * * *